US00PP11406P

United States Patent [19]

Verwer

[11] Patent Number: Plant 11,406

[45] Date of Patent: Jun. 6, 2000

[54] DAHLIA PLANT NAMED 'KARMA THALIA'

[75] Inventor: Aad Verwer, Lisse, Netherlands

[73] Assignee: Fa. Gebr. Verwer, Lisse, Netherlands

[21] Appl. No.: 09/026,005

[22] Filed: Feb. 19, 1998

[30] Foreign Application Priority Data

Apr. 7, 1997 [NL] Netherlands ..... DHL80

[51] Int. Cl.[7] ..... A01H 5/00

[52] U.S. Cl. ..... Plt./321

[58] Field of Search ..... Plt./321

[56] References Cited

PUBLICATIONS

GTITM UPOVROM Citation for 'Karma Thailia' as per NL PBR DHL0080; Apr. 7, 1997.

*Primary Examiner*—Howard J. Locker
*Assistant Examiner*—Kent L. Bell
*Attorney, Agent, or Firm*—Christie, Parker & Hale, LLP

[57] ABSTRACT

A dahlia plant variety producing red/purple flowers with the inner ray florets having an orange coloration which extends from the base up to about ⅓ of each ray floret.

1 Drawing Sheet

BACKGROUND OF THE INVENTION

The present invention relates to a new and distinct variety of *Dahlia hybrida* known by the varietal denomination 'Karma Thalia'. The female parent of 'Karma Thalia' is a variety known as 'Fuchsiana' and the male parent is the variety known as 'Stratos' both of which are unpatented undistributed varieties.

SUMMARY OF THE INVENTION

The new variety is a dahlia plant useful for growing outdoors and under glass which produces attractive red/purple flowers the inner ray florets having an orange coloration which extends from the base up to about ⅓ of each ray floret. Among the traits possessed by the new variety which in combination distinguish it from other varieties known to the inventor are its attractive flowers borne on long stems.

Asexual reproduction by cuttings of the new variety in The Netherlands has demonstrated that the combination of characteristics as described herein for 'Karma Thalia' are firmly fixed and are retained through successive generations of asexual reproduction.

COMPARISON WITH PARENTS

The new variety differs from its parents in flower color.

BRIEF DESCRIPTION OF ILLUSTRATION

The accompanying color photographic illustration shows a typical plant of the new variety in colors as nearly true as possible with an illustration of this type.

DESCRIPTION OF THE NEW VARIETY

In the following description, color references are to The Royal Horticultural Society Colour Chart, where color values refer to color plate numbers in this chart.

The following observations are of plants described and grown in The Netherlands under outdoor conditions which approximate those generally used in commercial practice.

'Karma Thalia' has not been observed under all possible environmental conditions. The phenotype may vary with variations in environment such as temperature, light intensity, day length and cultural conditions.

Parentage:

*Female parent.*—'Fuchsiana'.

*Male parent.*—'Stratos'.

Plant

*Form.*—Upright, spreading.

*Height.*—About 110 cm.

*Branching characteristics.*—Freely branching.

*Hardiness.*—Plants are winter hardy to 0° C.

*Natural flowering season.*—July to November in The Netherlands under glass.

*Disease resistance.*—Similar to the species.

*Flower stem.*—Length: About 70 cm. Color: Near 59A.

*Foliage.*—Quantity: Many. Shape of leaf: Ovate, base and apex are acute. Leaf edge: Serrate. Texture: Leaf upperside: Leathery. Leaf under side: Smooth. Color: Leaf upperside: Near 137B. Leaf under side: Near 148B. Venation: Pinnate. Petiole length: About 5 cm. Stipules: None. Stem color: Near 59A.

*Leaf arrangement and size.*—Opposite, single or compound, compound leaves of either 3 or 5 leaflets; leaf size single — about 11 cm long, about 5.5 cm wide; leaf size compound — about 24.8 cm long, about 14 cm wide.

Sepals:

*Numbers.*—About 15.

*Length.*—About 1.8 cm.

*Width.*—About 1.2 cm.

*Color.*—Near 137A.

*Base.*—Rounded.

*Apex.*—Broadly acute.

Bud:

*Form.*—Globular.

*Size.*—About 1 cm.

*Opening rate.*—About 14 days.

*Color of ray florets.*—When sepals first divide near 57B; when ray florets begin to unfurl near 57B.

Flower:

*Inflorescence.*—Form: Blooms borne singly. Type: Decorative. Diameter: About 12 to 13 cm. Number of flowers: About 50 to 60. Response: About 35 days from pinch.

*Color tonality from a distance.*—Red/violet.

*Lasting quality.*—About 14 to 19 days on plant; about 7 to 9 days after cutting.

Ray florets:

*Length*.—About 5.8 cm.

*Width*.—About 2.8 cm.

*Shape*.—Oblong.

*Apex*.—Obtuse.

*Base*.—Rounded.

*Color*.—Ray florets are red/purple with the inner ray florets having an orange coloration which extends from the base up to about ⅓ of each ray floret. Inner ray florets (upper surface and undersurface): Near 67A; Near 26B from the base up to about ⅓ of each ray floret. Outer ray florets (upper surface and undersurface): Near 67B. Point of ray floret attachment: Near 26B. As bloom ages: Colors fade to near 57C with strong streaking of near 26B. Fragrance: None.

Disc florets:

*Number*.—About 15.

*Length*.—About 1 cm.

*Color*.—Near 8A.

*Shape*.—Cylindric.

Reproductive organs:

*Stamens*.—Tubular, near 16A.

*Anthers*.—Small, near 16A.

*Pollen*.—Near 16A.

*Pistils*.—Styles length about 2 to 3 mm, color near 13B; stigmas divided, near 13B.

*Character of ovaries*.—1 per pistil.

I claim:

1. A new and distinct dahlia plant of the variety substantially as shown and described.

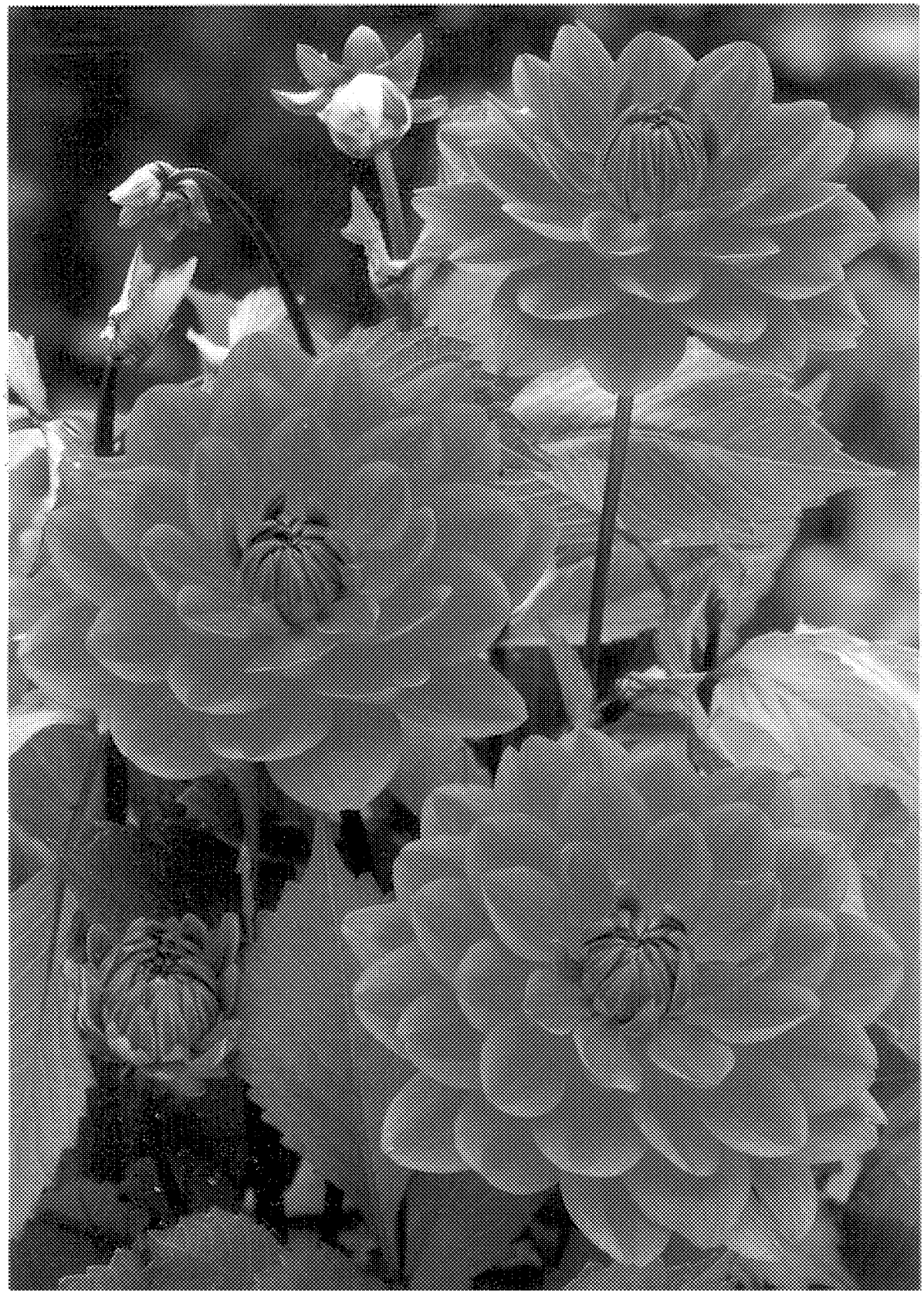

* * * * *